US006081267A

United States Patent [19]
Stockham et al.

[11] Patent Number: 6,081,267
[45] Date of Patent: Jun. 27, 2000

[54] COMPUTERIZED APPARATUS AND METHOD FOR DISPLAYING X-RAYS AND THE LIKE FOR RADIOLOGICAL ANALYSIS AND MANIPULATION AND TRANSMISSION OF DATA

[75] Inventors: Charles D. Stockham, Clarksville, Md.; Victor H. Levy, South Bend, Ind.; James F. McConkey, III, Reisterstown, Md.; Wayne Thornton DeJarnette, Phoenix, Md.; Dezso Csipo, Baldwin, Md.

[73] Assignees: Columbia Scientific Incorporated, Columbia; Dejarnette Research Systems, Inc., Towson, both of Md.

[21] Appl. No.: 09/195,936
[22] Filed: Nov. 19, 1998
[51] Int. Cl.[7] .................................. G06F 3/14; A61B 5/05
[52] U.S. Cl. .......................... 345/342; 345/334; 345/145; 345/339; 378/98; 378/98.2; 600/425
[58] Field of Search ..................................... 345/342, 340, 345/346, 334, 333, 145, 424; 600/425, 427, 410, 411; 378/4, 21, 98, 98.5, 98.2

[56] References Cited

U.S. PATENT DOCUMENTS

| | | | |
|---|---|---|---|
| 4,202,037 | 5/1980 | Glaser et al. | 345/354 |
| 5,060,170 | 10/1991 | Bourgeois et al. | 345/342 |
| 5,099,846 | 3/1992 | Hardy | 378/4 X |
| 5,274,759 | 12/1993 | Yoshioka | 345/439 X |
| 5,293,313 | 3/1994 | Cecil et al. | 382/131 |
| 5,452,416 | 9/1995 | Hilton et al. | 345/346 |

*Primary Examiner*—Raymond J. Bayerl
*Attorney, Agent, or Firm*—Leonard Bloom

[57] ABSTRACT

A computer apparatus and method for displaying radiological data such as X-rays, CT scans and other similar anatomical sequences in combination with other modalities such as plan views provides functionality which very closely resembles a standard radiological light box. Basic manipulations which occur at the light box by a radiologist or other medical personnel are closely emulated in function to allow medical personnel to stay focussed directly on the anatomical images and thereby avoid distraction and frustration of visually departing from the image in order to accomplish these basic functions. Some of the basic functions disclosed are quick-flip image mirroring, image rotation, panning, on-screen control of the number of images displayed in a mosaic, single drag and drop loading of radiological studies, cines and other functions. A dark and stark display further simulates the light box. A number of benefits and objectives are achieved in the disclosed embodiments which serve to illustrate the invention, in particular maximizing the time a radiologist or other medical personnel spend viewing images and minimizing time spent searching for controls or paging through software pages and pull-down menus.

14 Claims, 10 Drawing Sheets

COMPUTERIZED APPARATUS AND METHOD FOR DISPLAYING X-RAYS AND THE LIKE FOR RADIOLOGICAL ANALYSIS AND MANIPULATION AND TRANSMISSION OF DATA

BACKGROUND OF THE INVENTION

1. Field of the Invention

This invention pertains to the field of radiology generally, and more specifically to an improved apparatus and method for displaying radiological information such as anatomical images in a manner closely emulating light boxes, but having additional features and advantages available from computer image processing.

2. Description of the Related Art

Radiologists have traditionally reviewed X-ray photographic images on light boxes, sometimes also referred to as view boxes. These photographic images may be directly formed onto appropriate film stock by illuminating an anatomical region with X-ray radiation and then developing the film. Once developed, the film may be displayed directly on a light box. A radiologist will manually manipulate the images, including flipping the images top to bottom and left to right and also rotating the images, without looking away from the image. This is done by grasping an edge of the image and either flipping the image over to form a mirror image thereof or by rotating the image clockwise or counter-clockwise to view a rotated image. One image may be placed directly over another for visual comparison, and sequences are readily rearranged. Each of these manual actions is easy to perform and quite intuitive with the actual film stock. As a result, the film stock and light box is very convenient and easy to use, and most radiologists have grown accustomed to this system.

More recently, equipment has been developed which is capable of providing a radiologist and various other medical personnel with different views of the same physiology. Depending upon the symptoms a patient may present, imaging systems such as CT scans and/or MRI may be selected as appropriate diagnostic tools. Multiple images of sequential body sections may be generated, and duplicate sequences of the same body sections may be created with varying degrees of exposure intensity. By varying exposure intensity, a radiologist may be able to discern features from two contrasting sequences which might otherwise not be visible in either single sequence. These newer diagnostic imaging systems may generate electronic representations of the actual image, and these electronic signals may then be outputted to one or more media for viewing and storage. Often, even with electronic capability, the information from these newer diagnostic tools is outputted to transparencies for handling and review by the radiologist on the familiar light box.

Unfortunately, the radiologist loses some advantages that are inherent in the electronic system when the image is converted to "hard-copy" such as a transparency. Since the film stock is generally exposed at actual size, smaller details or features may be difficult to identify or interpret accurately. Images are not easily magnified to focus in on a particular feature, and special computer image processing features such as edge detect, sharpening and other techniques are unavailable. Furthermore, storage of images and sequences of images requires substantial filing space and expensive record archiving. Where a further review by other medical personnel is warranted, film stock is difficult to transmit and must be manually copied and delivered via a courier. The reviewing personnel are then also limited to views and magnification selected by the first reviewer. To further compound the challenges of hard-copy, many new diagnostic imaging systems are capable of generating hundreds of helpful, separate images in a single sequence. Handling the large quantities of images in hard-copy becomes quite cumbersome.

In an effort to circumvent the need for generating hard-copy, a number of computer systems have been developed which allow the radiologist to directly view the actual images for evaluation. These computer systems allow the radiologist to take advantage of a number of features available only through computer graphics presentation of the anatomical data, more commonly referred to as "soft-copy". Computer software is well known and widely available for performing a variety of image manipulation functions such as angular rotations, image flipping, edge detection, zooming or selective magnification, and sharpening. Unfortunately, much of the software was originally developed for graphic artists and others specializing in the development and manipulation of the content of images. In many cases, a radiologist does not need to create or substantially alter the image, but instead needs to be able to manipulate the image as easily and intuitively as possible. As a result of the differences between the way a graphic artist handles an image and the way a radiologist would handle the same image, many radiologists still prefer to work with film stock or computer generated transparencies and the traditional light box.

The prior art has disclosed various improvements which adapt the computer systems more specifically to the handling of anatomical data and for use by medical personnel, but these improvements are not completely satisfactory.

For example, Hilton et al in U.S. Pat. No. 5,452,416, incorporated herein by reference, proposes a multi-head workstation, meaning that more than one video display monitor is used to display radiological data. The system offers numerous features which are becoming more commonplace in radiological viewing systems, including database management, exam scheduling, fixed-site and mobile image input, case review, reporting, teleradiology, electronic delivery of images/reports (voice and text) to referring physicians' offices, printing, operation with LANs and WANs, integration with other information systems, automated image display based upon radiologists' individual preferences, automatic output based upon referring physicians' individual preferences, automated printing, and displaying of cines (cinematographic presentations of sequences of images).

Unfortunately, however, the Hilton et al system still requires a separate monitor on which a variety of menus and control icons are displayed. The additional monitor adds undesirable expense and desktop size to the system, but far more consequential than cost or space is the way a user must interface with the displays. For example, if when looking at an image, a radiologist identifies an area requiring more attention and wishes to put the image in different anatomical perspective, the radiologist must visually leave the area of interest, look at the separate monitor, find the necessary control to alter the image, and then return to the image on a different display screen. In leaving the radiological image, the radiologist is bound to lose track of the original area of interest and must locate the area once more. This can be a very frustrating waste of time, particular for those medical personnel who are accustomed to using the light boxes and film negatives, where the film may be grasped and manipulated without ever visually leaving the area of interest. As a result, many medical personnel still use hard-copy and resort to soft-copy viewing stations only for special applications and requirements.

A number of other systems are cited in the Hilton et al patent, each of which are also incorporated herein by reference for their enablement of the standard and basic features and functions necessary to implement a computerized radiological display system. Moreover, a number of these systems are available commercially that illustrate similar basic functionality. Nevertheless, none of these systems illustrates or teaches an apparatus or method which allows a user to truly emulate viewing film on a light box and still obtain additional benefits available only from soft-copy.

SUMMARY OF THE INVENTION

In a first manifestation of the invention, a computerized apparatus displays radiological anatomical data in the form of images that vary in type and preferred display formats. The apparatus allows an operator to stay visually focused on a display monitor where the images are displayed, and also provides a maximum display area for images. The invention comprises a display monitor screen with a graphical container therein where an image may be displayed; a cursor indicating a pointer position on the display monitor screen and having a variable position controlled by an operator input device; a frame control region within the graphical container which responds to pointer position and an additional operator input to change size of the graphical container and further control generation or removal of additional graphical containers, whereby reducing the graphical container size results in generation of additional graphical containers on the display monitor screen, while enlarging the first graphical container size results in removing additional graphical containers, thereby eliminating a need for an operator to progress through screen pages or pull-down menus or to move the cursor from the graphical container in order to initiate the change of size and generation or removal of additional graphical containers.

The invention also comprises a method for displaying a variable number of radiological images on a computer screen where a user may directly activate common functions and capabilities without accessing additional screen pages or pull down menus. This method comprises the steps of: defining a first image display region; presenting a handle within the image display region; indicating a cursor position; monitoring a cursor control input device for signals indicative of a change in desired cursor position; calculating cursor position based upon the signals; determining whether the cursor and handle overlap on the display; monitoring the cursor control input device for a signal indicative of cursor activation; varying the number of radiological images when the cursor and handle overlap, a signal indicative of cursor activation exists, and there is a change in desired cursor position; wherein the number of radiological images varies proportionally to a sign and magnitude of change in cursor position subsequent to cursor activation.

In a third manifestation, the invention is a method for rapidly switching between a multiple image mosaic display of radiological image data having a subimage displayed therein to and from a single image display of the subimage upon a display screen without moving a cursor from the subimage, comprising the steps of: defining an outside border within which the subimage display of radiological image data is displayed; establishing a control signal indicating user demand to convert between mosaic display and single image display; monitoring for occurrence of a control signal when the cursor is within the outside border; changing the display to mosaic display when the control signal occurs and a single image is displayed and to a single image display when the control signal occurs and a mosaic is displayed, whereby medical personnel may rapidly switch between standard displays for the medical imaging modalities including planar X-ray, CT and MRI while keeping the cursor on the subimage.

In a fourth manifestation, the invention is a method for manipulating an image display of radiological image data to a mirror image thereof without moving a cursor from the image and which emulates a manual motion used to flip film negatives, comprising the steps of: defining an outside border within which the image is displayed; defining an inner border within which the cursor will take a first displayed shape; changing the cursor to a second displayed shape when the cursor is between inner and outer borders; and mirroring the image when the cursor has the second displayed shape and a user generates a signal activating the cursor, whereby the cursor is positioned similarly with respect to the image to where a hand which flips film is positioned just prior to creating a mirror thereof.

The invention further comprises a method for manipulating an image display of radiological image data to a rotated image thereof without moving a cursor from the image and which emulates a manual motion used to rotate film negatives on a view box, comprising the steps of: defining an outside border within which the image is displayed; defining an inner border within which the cursor will take a first displayed shape; changing the cursor to a second displayed shape when the cursor is between inner and outer borders; and rotating the image in a direction of cursor movement when the cursor has the second displayed shape and a signal activates the cursor, whereby the cursor is positioned similarly with respect to the image to where a hand which rotates film is positioned and whereby cursor movement emulates a human hand during rotation of the image.

In a sixth manifestation of the invention, a dark and stark radiological image display apparatus closely emulates actions required of a radiologist reviewing film images on a view box by having direct and within the image cursor activation of view box functions and capabilities, and comprises the combination of: a display screen having icons thereon and otherwise void prior to activation of an image repository icon means for initiating display of a stored image sequence, the image repository icon means initiating the stored image sequence display responsive to a first cursor activation, whereby the display screen and image repository icon means emulate placement of film onto an empty view box; and a plurality of radiological image containers for displaying the stored image sequence, wherein each of the plurality of containers has an outer perimeter thereof responsive to a second cursor activation to cause a mirroring of a first image displayed therein, the outer perimeter further responsive to a third cursor activation to cause a rotation of the first image, whereby each of the containers emulate a single film exposure and closely emulate manipulation thereof by medical personnel; whereby preliminary screen pages and pull down menus which access functions normally performed by the radiologist directly with film images are eliminated, and the display screen is uncluttered by pull down menus, to thereby visually emulate film images on a view box.

OBJECTS OF THE INVENTION

A first object of the invention is to provide a computer apparatus and method for displaying radiological data which emulates function and preserves advantages of traditional film and view boxes. A further object of the invention is to reduce the complexity of a computer display apparatus. Another object of the invention is to improve the user interface, allowing a radiologist or other medical personnel to remain focused on an image while still performing basic functions. A still further object of the invention is to eliminate the myriad of pull down menus, pop up screens or hierarchical software pages in favor of intuitive control actions and icons. Yet a further object of the invention is to keep the display screen as dark and stark as possible, allowing maximum image display size and thereby more closely emulating a light box.

These and other objects of the invention are achieved in the preferred embodiment, which offers significant advantages over prior art systems.

DESCRIPTION OF THE PREFERRED EMBODIMENT

Figure 1A:
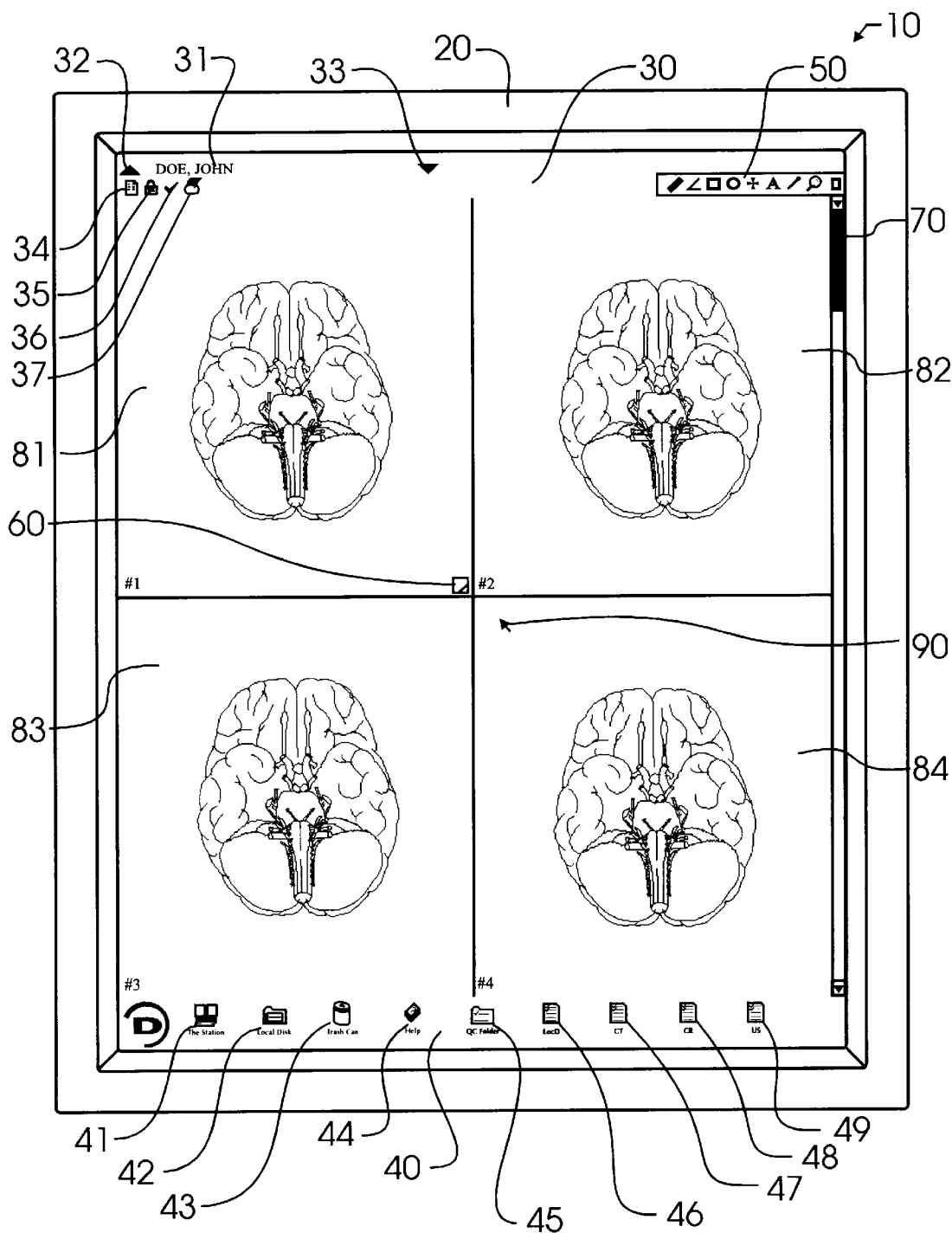
FIG. 1a illustrates a preferred embodiment mosaic display apparatus of the present invention.
Figure 1C:
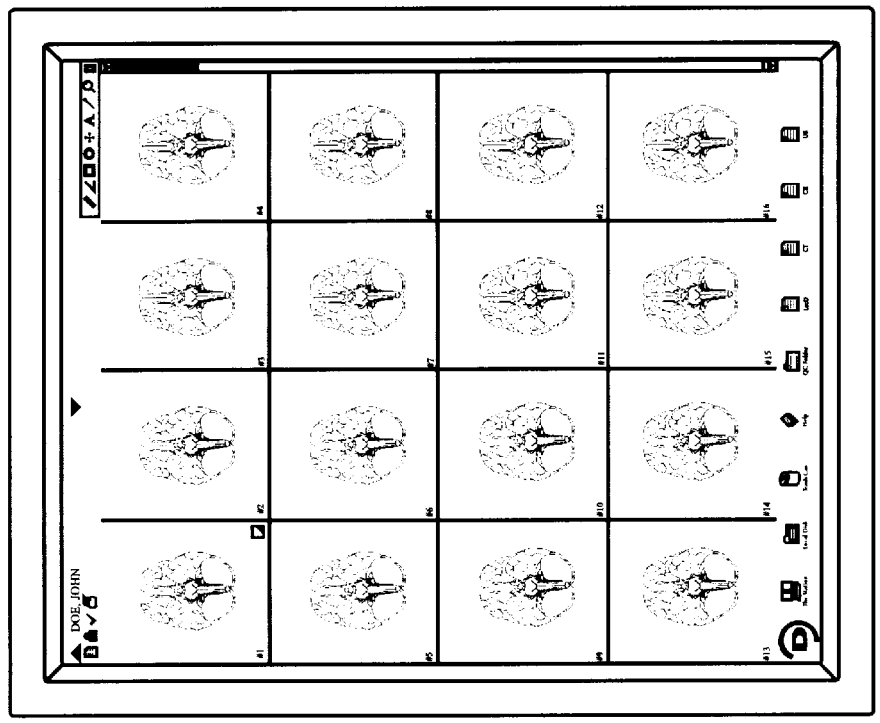
FIGS. 1b and 1c illustrate the quick-frame feature sequentially.
Figure 1B:
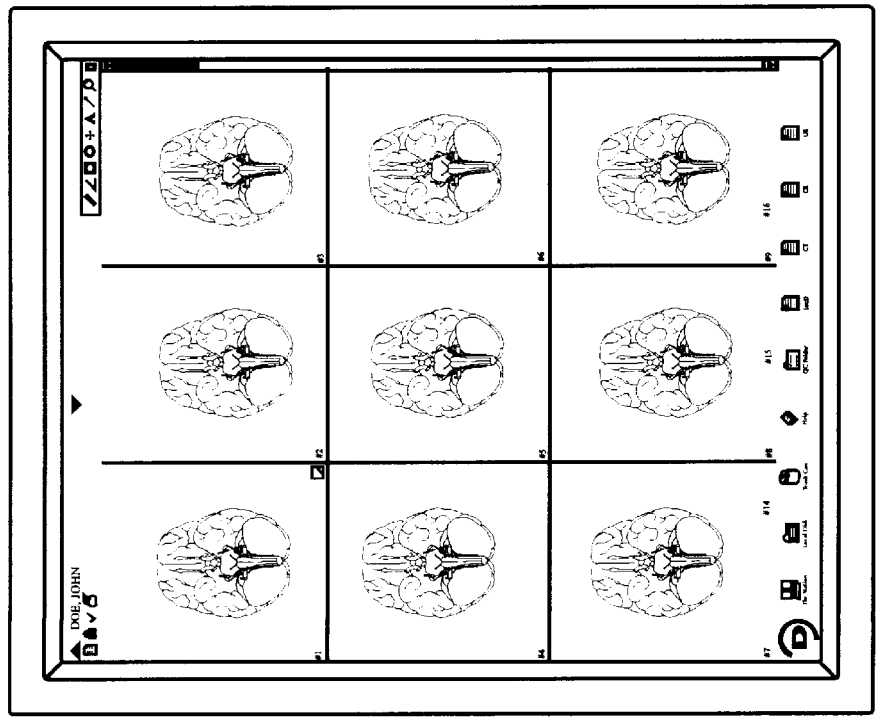

A preferred embodiment computerized apparatus for displaying radiological images in accord with the present invention is shown generally as apparatus 10 in FIG. 1. Apparatus 10 includes a display monitor 20 having a display screen 30 therein. At the bottom of display screen 30 is an icon bar 40 having a number of primary icons 41–49 therein. Each of these icons is used to initiate system functions and features, such as loading and unloading various studies or accessing help. At the top of display screen 30 there are a number of controls which are related to the specific study loaded on the display screen. The patient's name identifier 31 is found at the top left, and a number of alternater controls 32–37 are provided adjacent thereto. These controls 32–37 are used to advance to previous and subsequent studies, and to perform basic tasks such as printing, file linking and marking as read. An additional toolbar 50 is located at the top right of the screen, and contains a number of image analysis tools. Controls located therein provide tools for measurement of both linear distance and angle, rectangular ROI, elliptical ROI, pixel value, annotation, local image magnification and stacking (for cine generation). As shown in FIG. 1a, a 2×2 mosaic is displayed, showing a total of four image containers 81–84. The top left image container, 81 in this display of FIG. 1a, always has a small quick-frame control 60 in the lower right corner thereof. Quick frame control 60 is activated by moving cursor 90 onto control 60, and then pressing the left mouse down. A radiologist will then drag control 60 around display screen 30 to change the number of image containers displayed therein. For example, as shown in FIG. 1b, control 60 has been dragged diagonally up and left on display screen 60, to convert incrementally from a 2×2 mosaic to a 3×3 mosaic display. Once more, control 60 has ben dragged diagonally up and left from FIG. 1b to FIG. 1c, this time generating a 4×4 mosaic. The number of mosaic images available is practically limited by the resolution and display screen space available, and the space required to access control 60 with cursor 90. By providing control 60 in only one display container 81, a minimal amount of display screen 30 is used. Yet, the adjustment is easily made by an operator without having to look away from the images at hand.

In addition to increasing or decreasing the number of displayed images, a vertical scroll bar or elevator 70 is illustrated, which is present whenever there are additional images beyond those displayed in display screen 30 available for viewing. By scrolling this vertical scroll bar 70 up or down, previous or subsequent images will be displayed within containers 81–84.

This capability of performing light box functions without looking away from the images is referred to herein as "heads-up" work, where the operator doesn't have to resort to looking to a keyboard for special function keys or to a separate display monitor to perform a function. Moreover, the functions are accessible by placing the cursor directly within an image container such as container 81, thereby simplifying mouse movement to also keep the cursor within the image container. In the prior art systems, these basic functions require accessing different screens or software pages, pull-down menus, or special keys on the keyboard, any of which detracts from the actual review of the images, thereby adding time and contributing to user frustration and annoyance.

Figures 2A, 2B:
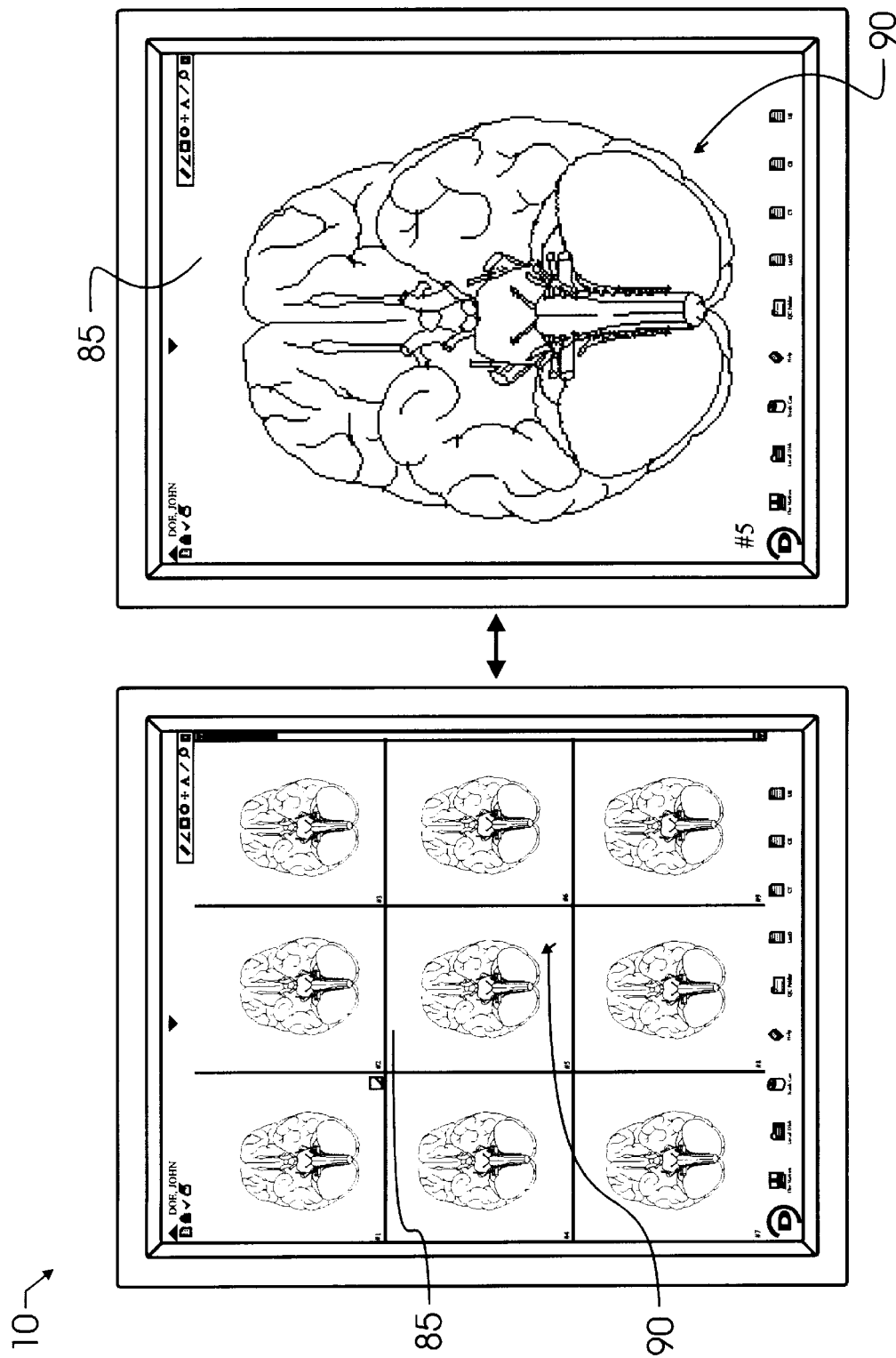
FIG. 2a illustrates a preferred embodiment mosaic display apparatus of the present invention and FIG. 2b illustrates the change from mosaic to single image display.

FIGS. 2a and 2b illustrate the process of enlarging any single display container, in this case image container 85, from within a mosaic display as shown in FIG. 2a to a single image, or "one-up" display as shown in FIG. 2b, and returning back to the mosaic. This conversion is accomplished by positioning cursor 90 over the desired image container, 85 in the present example, and then double clicking the left mouse button. Apparatus 10 will then display image container 85 in a full screen mode. Subsequently, double-clicking will restore the mosaic illustrated in FIG. 2a.

Figure 3C:
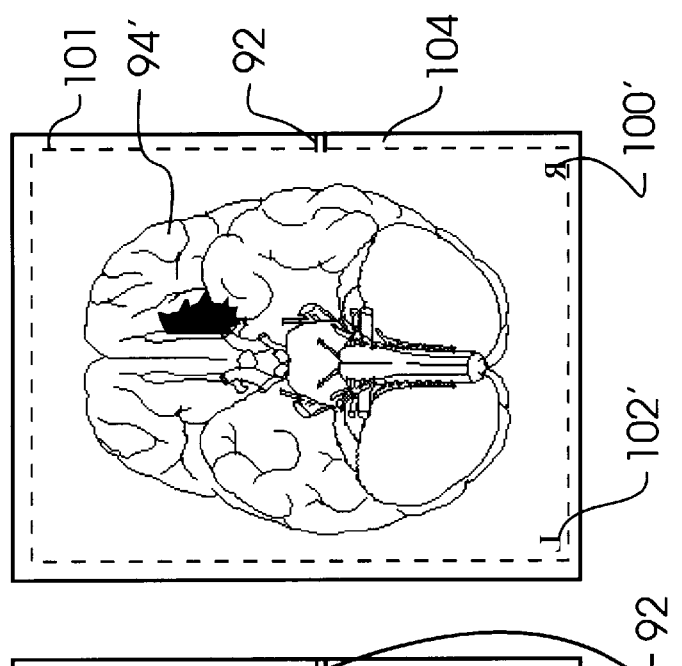
FIGS. 3a, 3b, and 3c illustrate the preferred embodiment quick-flip feature of the present invention, sequentially.
Figure 3B:
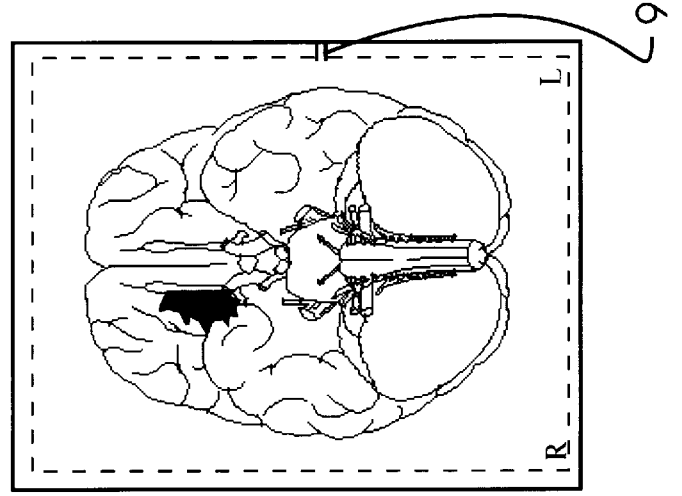
Figure 3A:
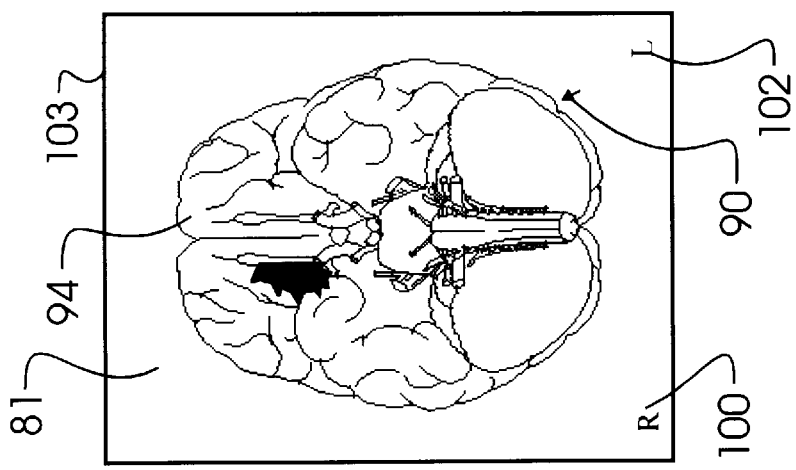

Mirroring an image on a light box is accomplished by simply grasping one edge of the film, and flipping the film over. To emulate this in the preferred embodiment of the invention (see FIGS. 3a–3c), container 81, which has an outer border 103 and contains an image 94, right indicator 100 and left indicator 102, and cursor 90 therein, is further subdivided by an inner border 101. When cursor 90 is moved from within inside inner border 101 to a perimeter region 104, cursor 90 will change shape to cursor shape 92 (as shown in FIG. 3b). Any cursor shape will be suitable, as is well known in the art. However, the parallel lines are preferred in the present embodiment. Next, by simply clicking on the left mouse button, image 94 will be mirrored within image container 81, as is shown in FIG. 3c, to form mirrored image 94'. As is evident, right indicator 100 and left indicator 102 are also mirrored to new indicators 100' and 102', respectively. Once again, the emulation of flipping a film on a light box is very closely emulated by moving the mouse to the perimeter, just as an operator would move their hand, and the actual flipping is emulated by a simple mouse click. The operator may stay visually focussed on the displayed image 94, without ever leaving the image to achieve the mirror function.

Figure 4A:
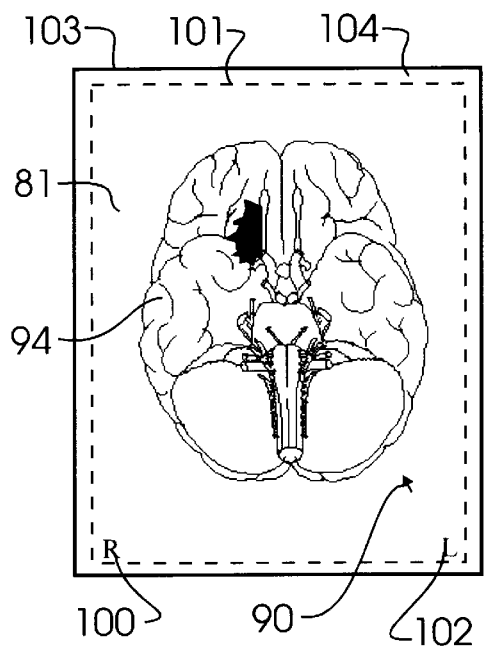
FIGS. 4a, 4b, 4c and 4d illustrate the image rotation feature of the present invention, sequentially.
Figure 4B:
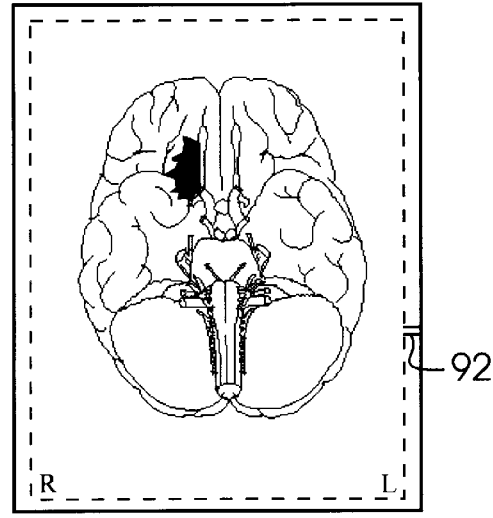
Figure 4C:
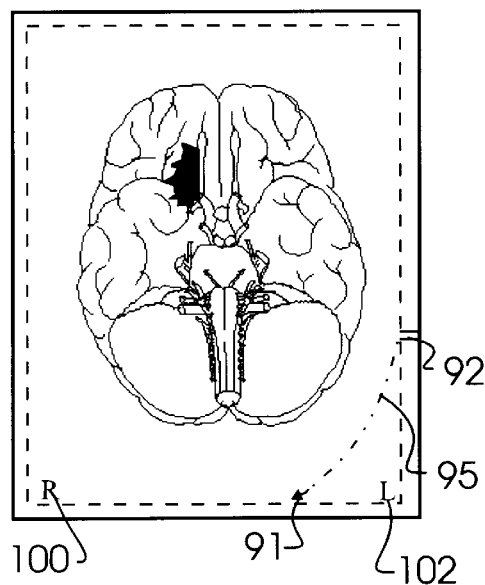
Figure 4D:
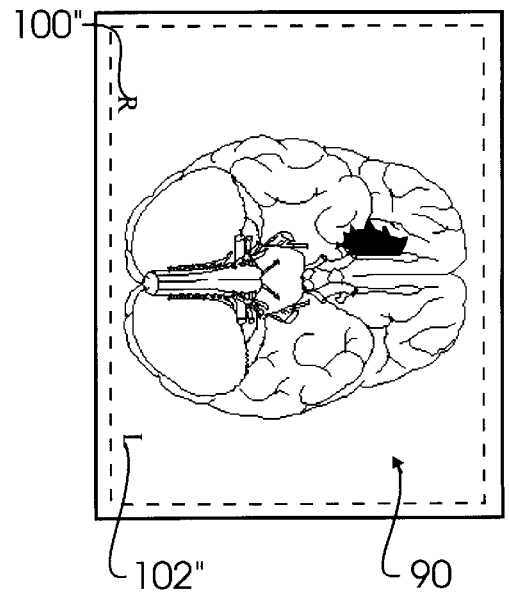

Illustrated by sequential FIGS. 4a–4d is the image rotation feature. Similar to the quick flip feature of FIGS. 3a–3c, cursor 90 is moved into perimeter 104. Once in perimeter 104, apparatus 10 will change the displayed cursor shape to new cursor 92 (FIG. 4b). Next, as shown in FIG. 4c, an operator will click the left mouse button down and begin to drag cursor 92 towards a different part of image container 81, as if the operator were grasping the film stock and spinning it about a center point. One exemplary path for cursor 92 is shown in FIG. 4c as path 95. When cursor 92 has traversed enough of container 81, the exact amount which is not critical and may be determined during design of apparatus 10 or by adjustable preset default values, cursor 92 will change to cursor 91, which is a curved arrow (FIG. 4c). Dropping cursor 91 will rotate image 94 within container 81, as shown in FIG. 4d. So long as cursor 91 is once again within inner border 101, cursor 91 will revert back to cursor 90 at the same time, as shown in FIG. 4d. With the rotation, right and left indicators 100 and 102 will also be rotated to become new rotated indicators 100' and 102", respectively.

Figure 5:
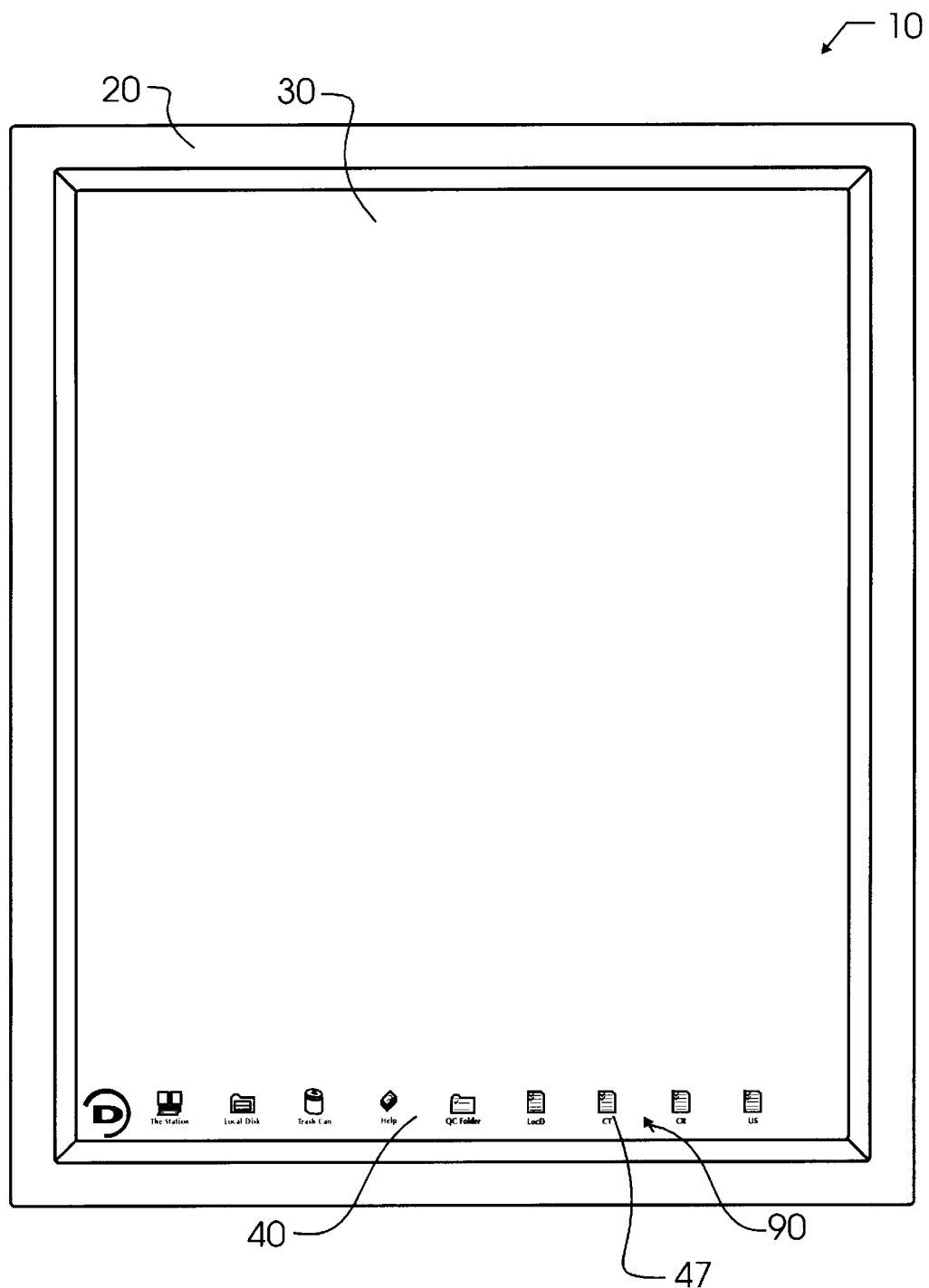
FIG. 5 illustrates the dark and stark interface of the preferred embodiment apparatus prior to loading any studies.

FIG. 5 illustrates the dark and stark appearance of the present invention, prior to loading any studies into display screen 30. For sake of illustration, the standard line drawings have been used with a white paper background. However, in actual practice of the invention in the preferred embodiment, display screen 30 will be black and icons 41–49 therein will be illuminated. While other background and foreground colors are possible, a black background is preferred for several reasons. By using the black background, apparatus 10 including monitor 20 and display screen 30 may be left on continuously, twenty-four hours each day. Phosphor burning will not be a serious problem, since display screen 30 will remain primarily dark. To load a study, an operator will not need to look away from display screen 30 or work through a long sequence of additional software pages. The operator must simply position cursor 90 over an appropriate icon, for example icon 47, and then drag and drop icon 47 towards the center of display 30. Apparatus 10 will then initiate loading and displaying the studies that have been stored with the associated icon. Once again, full time and attention of the operator is directed to the display screen 30, and not to a series of distracting and frustrating intermediate pages or menus. Nearly the entire display screen area 30 is preserved for display of a study, since there are many fewer icons or controls required in the preferred embodiment than were previously required by the prior art.

Figure 6:
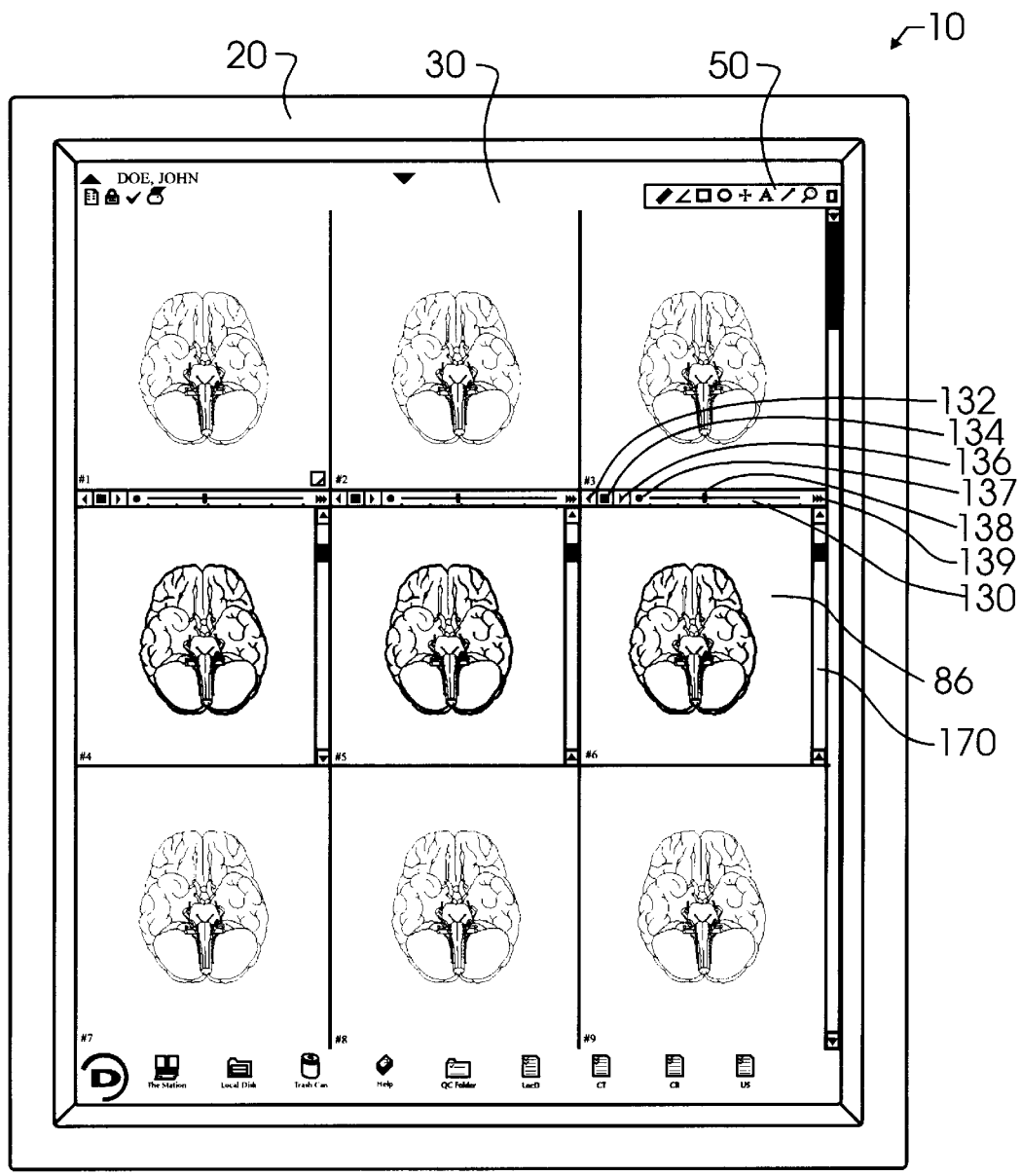
FIG. 6 illustrates the preferred embodiment apparatus with several cine displays active.
Figure 7:
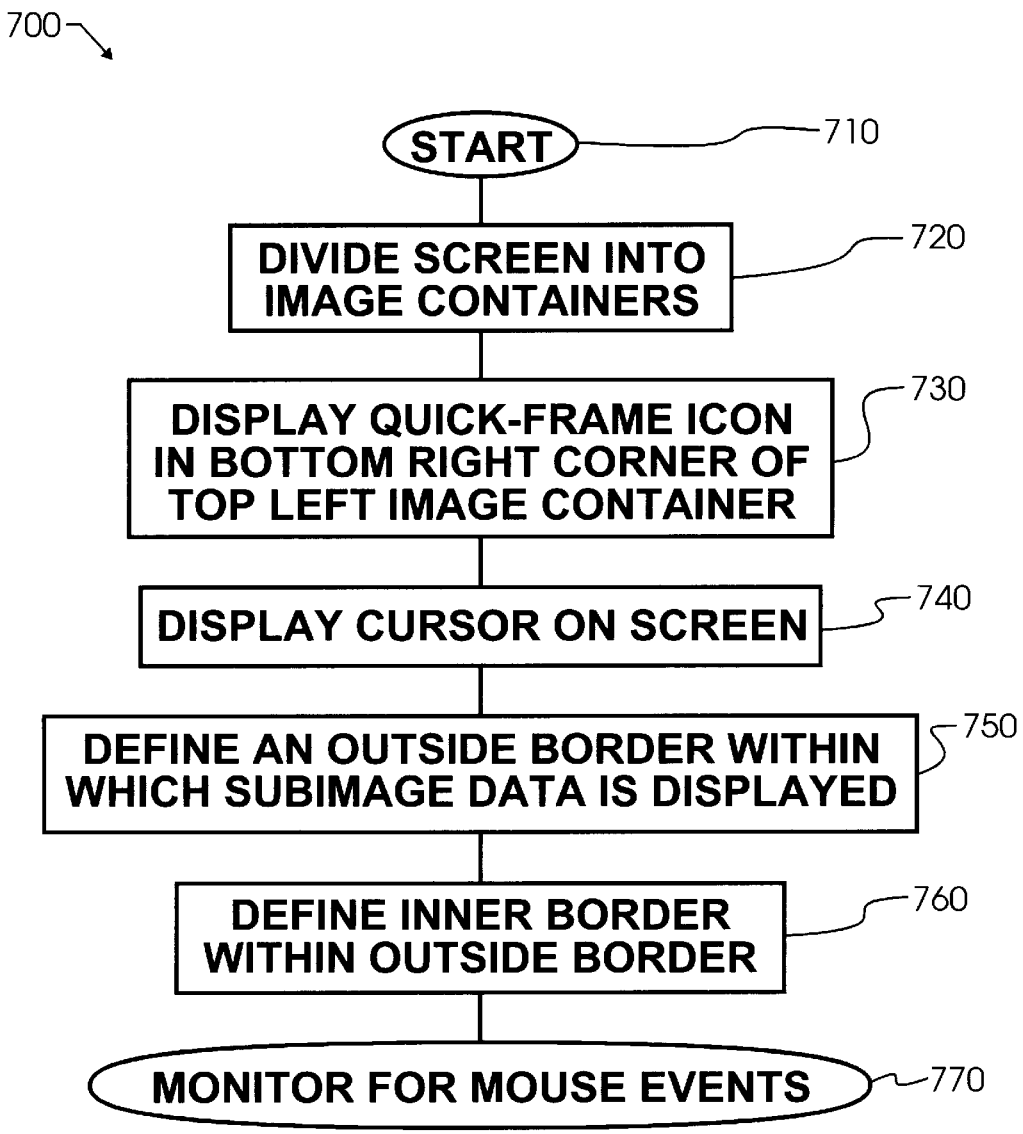
FIG. 7 is a flow chart which illustrates various initialization steps of a preferred embodiment of the present invention.
Figure 8:
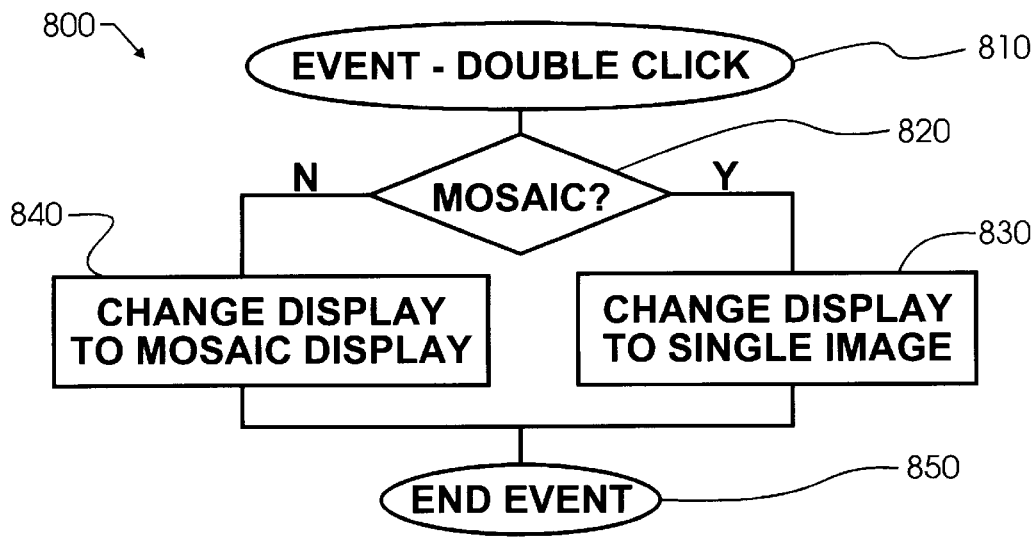
FIG. 8 is a flow chart which illustrates the various steps of the preferred embodiment change from mosaic to single image display.

FIG. 6 illustrates apparatus 10 with several cines, or cinematographic sequences, running within individual image containers. Implementation of the cine is achieved by dragging and dropping the cine tool from within tool bar 50 onto the image container, in which case all images within the series will be sequenced. Once the cine tool was dragged and dropped onto a frame, control of the cine is achieved through controls 132–139 on cine frame bar 130. As shown in FIG. 6, image container 86 has a horizontal bar at the top of container 86 which is used to start, stop, or control the sequence speed through a variable slider. Vertical scroll bar 170 is also provided, and performs function similar to scroll bar 70 of FIG. 1, wherein images may be scrolled through, from the first in the sequence to the last. Other functions may be accessed through, for example, a right mouse click and pop-up menu, such as looping, synchronization of multiple cine frames, and specific rate displays. The cine functions are readily implemented by those skilled in the art. Nevertheless, the present invention illustrates a method of implementation for the primary functions which does not require access to additional software pages, thereby conforming to the objectives of the present invention.

FIGS. 7–10 illustrate by flow chart a set of steps for implementing some of the features of the present invention. Those skilled in the art will recognize at once that these flow charts are vastly simplified in order to focus solely on the features of the present invention, and that there will be many more activities required for a full system implementation, some which may result in minor differences in the present flow charts. Nevertheless, the flow charts serve to illustrate various components of one embodiment of the features of the present invention.

Sequence 700 (FIG. 7) illustrates a basic display screen set-up sequence to establish image containers in step 720, place the quick-frame icon in step 730, display the cursor on screen in step 740, and define image container inner and outside borders at steps 750 and 760. Those skilled in the art will recognize that the actual order of these steps may be varied and that other activities will also occur which are not illustrated herein, such as actual display of images from a radiology study. Nevertheless, these steps in sequence 700 define basic structures which are required for further processing of the preferred embodiment.

Sequence 800 (FIG. 8) illustrates several basic computations required to process the conversions illustrated in FIGS. 2a and 2b. As shown in step 810, an input device such as a computer mouse must be monitored. Often this is achieved through interrupt processing, wherein the input will temporarily interrupt other processing by a CPU, and the CPU will then run a small control loop as established by the software. In the present invention, a mouse double-click, or the equivalent signal indicating activation of the cursor as selected by a programmer or hardware purchaser, will be monitored for sequence 800. If double click event 810 occurs while cursor 90 is within the inner border 101 of an image container, then sequence 800 will be activated and processing will proceed to step 820. Step 820 will determine whether a mosaic is presently displayed. If a mosaic is displayed, processing proceeds to step 830, and, if not, processing instead proceeds to step 840. At step 830, the display screen will be changed to display the single image within which the double click occurred, at full screen mode. At step 840, alternatively, the single image will be converted back to a mosaic. Once the appropriate step 830 or 840 is processed, the event processing is completed and programming will return to other processing as dictated by the remaining software and hardware.

Figure 9:
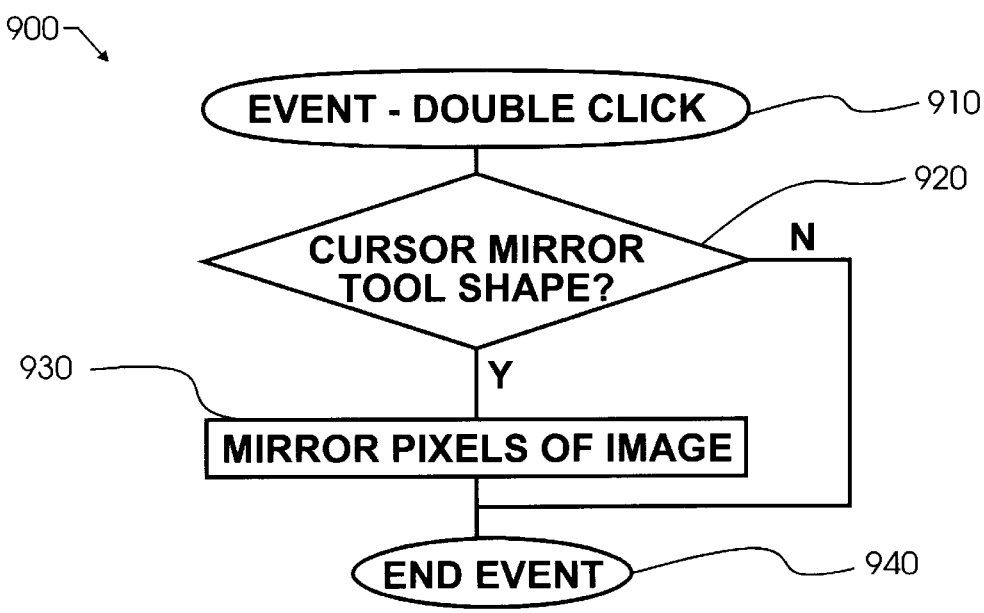
FIG. 9 is a flow chart which illustrates the various steps of the preferred embodiment quick-flip feature of the present invention.

In sequence 900 of FIG. 9, a double click will also be tested, and if it occurs within the outer perimeter 104 of an image container, in this case illustrated by determining whether the cursor is a mirror tool shape at step 920, the event processing of sequence 900 will proceed to step 930. Therein, the pixels within the image container will be mirrored through the implementation of well known and available software code. If the cursor is not in the outer perimeter 104 and so does not have the mirror tool shape, the image will not be mirrored.

Figure 10:
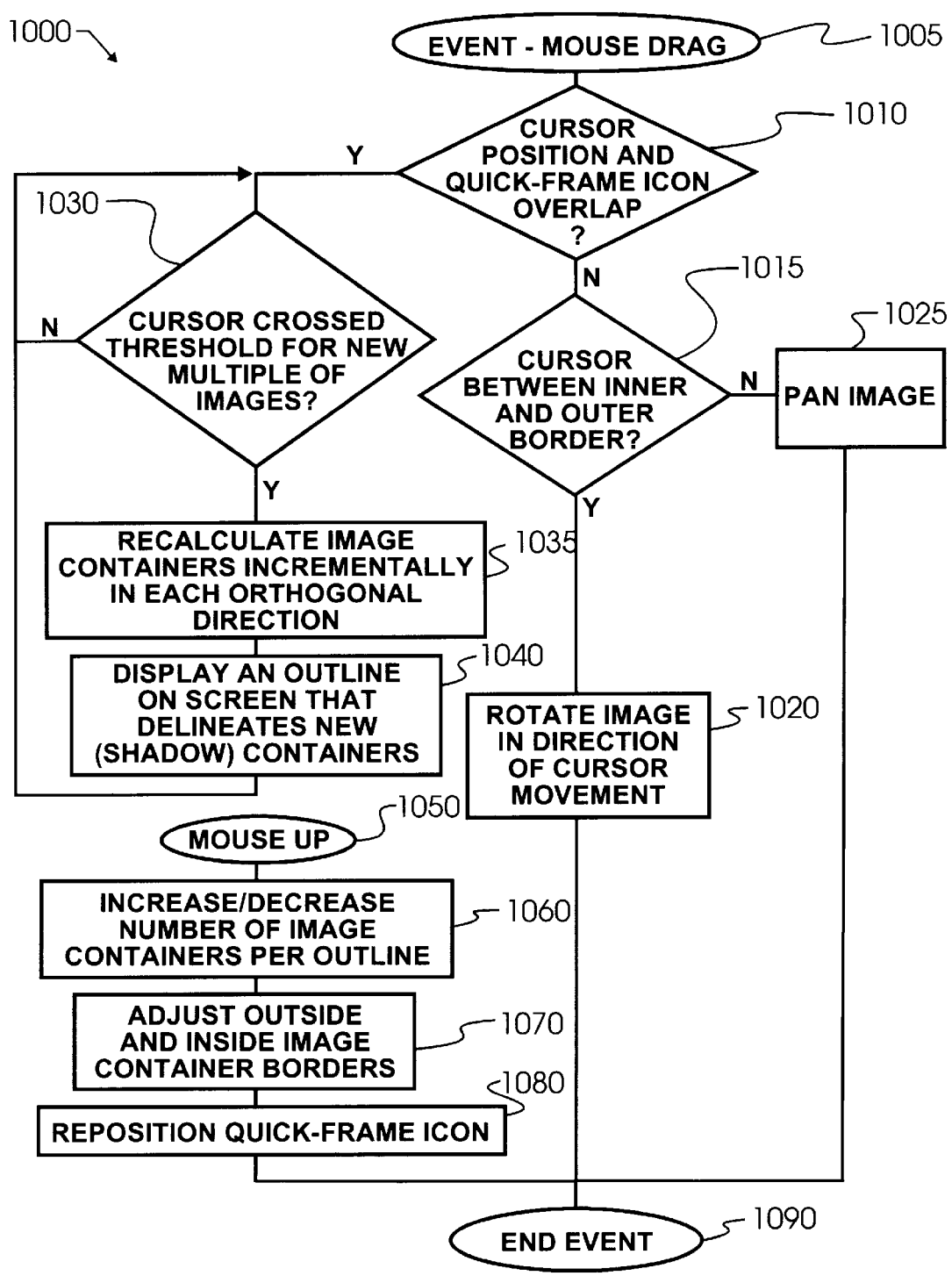
FIG. 10 is a flow chart which illustrates the various quick-frame and rotate steps of the preferred embodiment of the present invention.

In sequence 1000 of FIG. 10, a mouse drag interrupt is processed beginning with step 1005. The cursor position is determined, and in step 1010 overlap is determined between the cursor position and icon. If there is overlap, signified by the Y or yes sequence to step 1030, then the quick-frame sequence is activated. At this point, a loop is initiated through steps 1030, 1035, and 1040 until a further interrupt occurs by releasing the mouse button as shown at step 1050. Within the loop of steps 1030–1050, cursor position is monitored to determine whether cursor 90 has crossed a threshold for creating a new multiple of images. As long as this has not occurred, and the mouse up event has not occurred, then processing stays with step 1030 monitoring the position of cursor 90. Once a threshold is crossed, then processing proceeds to step 1035. Therein, the number of image containers is incremented or decremented in each orthogonal direction, depending upon which threshold was crossed. Next, in step 1040 an outline or layout guide is displayed on display screen 30 that delineates a proposed set of outer borders for a new mosaic. Once the shadow outlines are displayed, processing returns to step 1030 to once again monitor cursor position. The final change in numbers of image containers occurs when a mouse-up event occurs as shown by step 1050. At this time, the image containers are actually changed, as shown in step 1060. New outside and inside borders are calculated in step 1070, and the quick frame icon must be repositioned as shown in step 1080. Once again, the specific sequence of these steps in not critical, so long as the individual steps are actually implemented. Once the final processing of the mouse-up event through step 1080 is completed, processing returns to other programs as illustrated by end event step 1090.

If cursor 90 and quick frame icon 60 do not overlap in step 1010, then processing proceeds to step 1015, where the cursor position is evaluated with respect to inner and outer borders 101 and 103. If cursor 90 is within inner border 101 in step 1015, then processing proceeds to step 1025, which institutes a standard image panning within the image container. Alternatively, if cursor 92 is in an outer perimeter 104, then processing proceeds to step 1020, where, after the cursor is dropped, image 94 will be rotated in the direction of cursor movement. In the preferred embodiment, image 94 may be rotated 180 degrees if cursor 91 is moved past a center of image 94 to a half of image 94 opposite where cursor 92 originated.

While the foregoing details what is felt to be the preferred embodiment of the invention, no material limitations to the scope of the claimed invention are intended. Further, features and design alternatives that would be obvious to one of ordinary skill in the art are considered to be incorporated herein. For example, activating signals may be received as mouse clicks or double clicks from either left or right mouse buttons, or from other input devices or other buttons as may be created or provided for during design of apparatus in accord with the present invention. The critical factor is that the event be separately monitored and discernable from the cursor position. The mouse input is a preferred embodiment, since single hand control, standard hardware and easy familiarity are all benefits thereof. Other variations are contemplated for the invention and would be obvious to those of ordinary skill in the art, such as any of a multitude of different icon and cursor designs and shapes. With this in mind, the scope of the invention is set forth and particularly described in the claims hereinbelow.

What is claimed is:

1. A computerized apparatus for displaying radiological anatomical data in the form of images that vary in type and preferred display formats which allows an operator to stay visually focused on a display monitor where said images are displayed, and also provides said operator with a maximum display area for said images, comprising:
    a display monitor screen with a first graphical container therein where a first one of said images may be displayed;
    a cursor indicating a pointer position on said display monitor screen, said pointer position variable and controlled by an operator input device;
    a frame control region within said first graphical container which responds to said pointer position and an additional operator input to change a size of said first graphical container and further control generation or removal of additional graphical containers, whereby reducing said first graphical container size results in generation of said additional graphical containers on said display monitor screen, while enlarging said first graphical container size results in removing said additional graphical containers, thereby eliminating a need for said operator to progress through screen pages or pull-down menus or to move said cursor from said first graphical container in order to initiate said change of size and generation or removal of said additional graphical containers.

2. The computerized apparatus for displaying radiological anatomical data of claim 1 wherein said additional operator input is a left mouse button down signal.

3. The computerized apparatus for displaying radiological anatomical data of claim 1 wherein said pointer position must be on said frame control region to initiate said change of size.

4. The computerized apparatus for displaying radiological anatomical data of claim 1 wherein said operator input device comprises a mouse.

5. The computerized apparatus for displaying radiological anatomical data of claim 1 wherein said change of size occurs discontinuously.

6. The computerized apparatus for displaying radiological anatomical data of claim 5 wherein each discontinuous size change is displayed upon said display monitor screen with a shadow grid, thereby enabling said operator to determine how many graphical containers will be displayed while continuously visually focussing on said display monitor.

7. The computerized apparatus for displaying radiological anatomical data of claim 1 wherein said frame control region is represented by a small icon within said first graphical container.

8. The computerized apparatus for displaying radiological anatomical data of claim 7 wherein said first graphical container is rectangular and said small icon is in a corner of said first graphical container.

9. The computerized apparatus for displaying radiological anatomical data of claim 1 wherein said first graphical container size may be enlarged until no additional graphical containers are displayed on said display monitor screen and only said first graphical container is displayed.

10. A method for displaying a variable number of radiological images on a computer screen where a user may directly activate common functions and capabilities without accessing additional screen pages or pull down menus, comprising the steps of:
    defining a first image display region within said screen;
    presenting a handle within said image display region;

indicating a cursor position on said screen;

monitoring a cursor control input device for signals indicative of a change in desired cursor position;

calculating said cursor position based upon said signals indicative of a change in desired cursor position;

determining whether said cursor position and said handle overlap;

monitoring said cursor control input device for a signal indicative of cursor activation;

varying said number of radiological images when said step of determining yields overlap, said step of monitoring cursor activation yields said signal indicative of cursor activation, and said step of monitoring desired cursor position yields signals indicative of said change in desired cursor position wherein said number of radiological images varies proportionally to a sign and magnitude of change in cursor position subsequent to an initiation of said signal indicative of cursor activation.

11. The method for displaying a variable number of radiological images on a computer screen of claim 10 wherein said step of defining further comprises displaying an outline on said screen which delineates regions where said variable number of radiological images will be displayed.

12. The method for displaying a variable number of radiological images on a computer screen of claim 10 wherein said radiological images are varied in number based upon incremental increases or decreases in each of two orthogonal directions.

13. A method for rapidly switching between a multiple image mosaic display of radiological image data having a subimage displayed therein to and from a single image display of said subimage upon a display screen without moving a cursor from said subimage, comprising the steps of:

defining an outside border within which said subimage display of radiological image data is displayed;

establishing a control signal indicating user demand to convert between mosaic display and single image display;

monitoring for occurrence of said control signal when said cursor is within said outside border;

changing said display to said mosaic display when said control signal occurs and said single image is displayed and to said single image display when said control signal occurs and said mosaic is displayed, whereby medical personnel may rapidly switch between standard displays for the medical imaging modalities including planar X-ray, CT and MRI while keeping said cursor on said subimage.

14. The method for rapidly switching of claim 13 wherein said control signal is a mouse-type double-click.

* * * * *